US00PP30773P2

(12) United States Plant Patent
Klemm et al.

(10) Patent No.: US PP30,773 P2
(45) Date of Patent: Jul. 30, 2019

(54) ***LOBELIA* PLANT NAMED 'KLELE17018'**

(50) Latin Name: *Lobelia erinus*
Varietal Denomination: KLELE17018

(71) Applicant: Klemm+Sohn GmbH & Co. KG, Stuttgart (DE)

(72) Inventors: Nils Klemm, Stuttgart (DE); Ulrich Lohmüller, Groβhabersdorf (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,958

(22) Filed: May 30, 2018

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./451
See application file for complete search history.

*Primary Examiner* — Anne Marie Grunberg
(74) *Attorney, Agent, or Firm* — Barbara Campbell; Cochran Freund & Young LLC

(57) ABSTRACT

A new *Lobelia* plant particularly distinguished by purple flowers with white centers, and a semi-upright and freely branching growth habit, is disclosed.

1 Drawing Sheet

Genus and species: *Lobelia erinus.*
Variety denomination: 'KLELE17018'.

BACKGROUND OF THE NEW PLANT

The present invention comprises a new and distinct variety of *Lobelia*, botanically known as *Lobelia erinus*, and hereinafter referred to by the variety name 'KLELE17018'. 'KLELE17018' originated from a controlled hand-pollination in June 2013 in Stuttgart, Germany between the proprietary female *Lobelia* variety 'LE-2009-1047' (unpatented) and the proprietary male *Lobelia* variety 'LE-2011-0079' (unpatented).

The seeds from the cross were sown and plants were grown in a greenhouse for evaluation, where an individual plant designated 'KLELE17018' was selected from the group. In 2014, 'KLELE17018' was first vegetatively propagated via vegetative cuttings. 'KLELE17018' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Purple flowers with white centers; and
2. A semi-upright and freely branching growth habit.

DESCRIPTION OF THE PHOTOGRAPH

This new *Lobelia* plant is illustrated by the accompanying photograph which shows the plant's overall plant habit including form, foliage, and flowers. The photograph is of a 7-week-old plant grown in a glass greenhouse in 10-centimeter with a pinch date one week prior potting and cool morning, in Stuttgart, Germany in April 2018.

The colors shown are as true as can be reasonably obtained by conventional photographic procedures.

DESCRIPTION OF THE NEW VARIETY

The following detailed descriptions set forth the distinctive characteristics of 'KLELE17018'. The data which define these characteristics were collected from asexual reproductions carried out in Stuttgart, Germany. Data was collected on 7-week-old plants grown in a greenhouse in Stuttgart, Germany in April 2018. Color references are to The R.H.S. Colour Chart of The Royal Horticultural Society of London (R.H.S.), 5$^{th}$ edition (2007).

Classification:
- *Family.*—Campanulaceae.
- *Botanical.*—*Lobelia erinus.*
- *Common.*—*Lobelia.*
- *Designation.*—'KLELE17018'.
- *Parentage.*—Female parent: The proprietary female *Lobelia* variety 'LE-2009-1047' (unpatented). Male parent: The proprietary male *Lobelia* variety 'LE-2011-0079' (unpatented).

Growth:
- *Growth and branching habit.*—Semi-upright, freely branching.
- *Form.*—Rounded to flat.
- *Height* (*measured from the top of the soil including any flowers*).—10.5 cm.
- *Width* (*horizontal plant diameter, including any flowers*).—24.0 cm.
- *Time to produce a finished flowering plant.*—8 weeks.
- *Outdoor plant performance.*—Very good.
- *Time to initiate roots.*—18 days.
- *Root description.*—Fine, white roots, freely branching, and dense.

Leaves:
- *Arrangement.*—Alternate.
- *Color.*—Immature Leaf: Upper surface: RHS 137A (Green). Lower surface: RHS 137C (Green). Mature Leaf: Upper surface: RHS 139A (Green). Lower surface: RHS 139C (Green).

*Length*.—4.0 cm to 5.0 cm.

*Width*.—1.0 cm to 1.6 cm.

*Shape*.—Ovate to lanceolate.

*Margin*.—Serrate.

*Apex*.—Sub-obtuse.

*Base*.—Acute.

*Texture* (*both surfaces*).—Smooth.

*Venation*.—Pinnate.

Stems:

*Length*.—12.0 cm.

*Diameter*.—0.2 cm.

*Internode length*.—0.9 cm to 1.2 cm.

*Texture*.—Smooth.

*Stem anthocyanin*.—Absent.

*Peduncle*.—Length: 2.2 cm to 3.2 cm. Diameter: 0.8 cm. Texture: Smooth.

Flower buds:

*Shape*.—Inverse drop-shaped.

*Diameter*.—0.3 cm.

*Length*.—0.8 cm.

Inflorescence:

*Blooming habit*.—Continuous.

*Lastingness of individual blooms on plant*.—Approximately 1 week.

*Fragrance*.—Absent.

*Inflorescence type*.—Raceme.

*Quantity of flowers and buds per flowering branch*.—15 to 20.

Flowers:

*Flower diameter* (*horizontal*).—2.0 cm.

*Flower height* (*vertical*).—1.7 cm.

*Mature flower*.—Upper lobe: Color, upper surface: RHS 155D (White) in the central region and RHS N81A (Purple-violet) for the remainder of the petal. Color, lower surface: RHS 84A (Violet) to RHS 84C (Violet). Length: 1.0 cm. Width: 0.7 cm. Shape: Obovate. Apex: Obtuse. Margin: Entire. Texture (both upper and lower surfaces): Smooth. Lower lobe: Color, upper surface: RHS N81A (Purple-violet). Color, lower surface: RHS 84A (Violet). Length: 0.6 cm. Width: 0.15 cm. Shape: Obovate. Apex: Obtuse. Margin: Entire. Texture (both upper and lower surfaces): Smooth.

*Corolla tube*.—Color inside: RHS 155C (White) with RHS 72B (Red-purple) pattern. Color outside: RHS 155C (White) with RHS 84B (Violet) pattern. Tube length: 0.7 cm. Diameter: 0.2 cm at the bottom, 0.4 cm at the top.

*Calyx*.—Length: 1.2 cm (0.4 cm for the fused part, 0.6 cm for the non-fused part). Diameter: 0.2 cm. Shape: Funnel, star-shaped with fused sepals in lower half. Apex: Acute. Texture: Smooth. Color: RHS 137C (Green) for the fused part and RHS 139A (Green) for the non-fused part of the upper surface; RHS 139A (Green) anthocyanin.

Reproductive organs:

*Stamens*.—Quantity per flower: 5. Filament length: 0.5 cm. Filament color: RHS 79B (Purple) at the top, RHS 155D (White) at the base. Anther length: 0.2 cm. Anther width: 0.08 cm. Anther color: RHS 200A (Brown). Pollen amount: Medium. Pollen color: RHS 154D (Yellow-green).

*Pistils*.—Quantity per flower: 1. Pistil length: 1.1 cm. Stigma shape: Discoid. Stigma color: Immature: RHS 79A (Purple). Mature: RHS 200A (Brown) in the center and RHS 155D (White) for the outer part. Style length: 0.7 cm. Style color: RHS 144B (Yellow-green). Ovary color: RHS 144B (Yellow-green).

Fruit and seed set: Fruit and seed set not observed.

Disease and pest/insect resistance: No disease and pest/insect resistance observed.

COMPARISON WITH PARENTAL LINES AND KNOWN VARIETY

'KLELE17018' can be distinguished from its parents as described in Table 1.

TABLE 1

Comparison with Parental Lines

| Characteristic | 'KLELE17018' | Female Parent 'LE-2009-1047' | Male Parent 'LE-2011-0079' |
|---|---|---|---|
| Color | Purple | Lavender | Purple |
| Growth habit | Semi-upright | Compact and upright | Upright |

'KLELE17018' is most similar to the commercial *Lobelia* variety 'KLELE11769' (U.S. Plant Pat. No. 24,037). Differences between the varieties are described in Table 2.

TABLE 2

Comparison with Similar Variety

| Characteristic | 'KLELE17018' | 'KLELE11769' |
|---|---|---|
| Color | Purple | White |
| Growth habit | Semi-upright | Basket-like |

We claim:

1. A new and distinct variety of *Lobelia* plant designated 'KLELE17018' as shown and described herein.

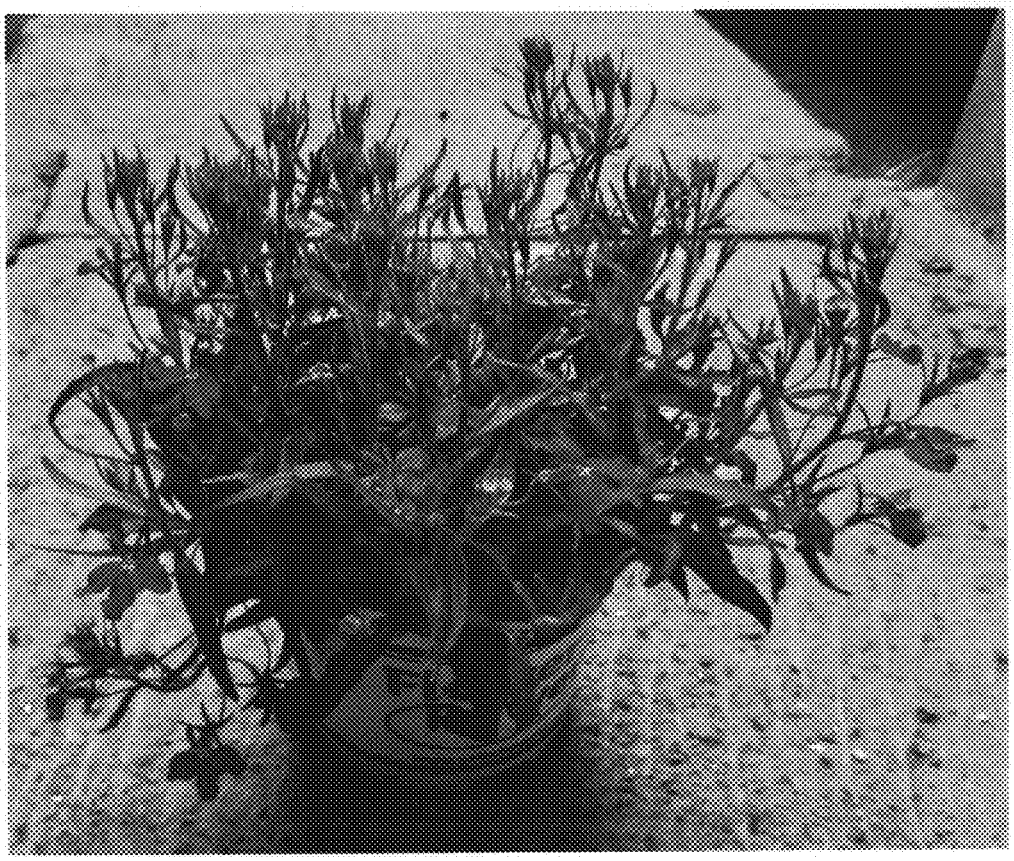

* * * * *